United States Patent
Hennessey et al.

(10) Patent No.: US 9,811,158 B2
(45) Date of Patent: Nov. 7, 2017

(54) SYSTEM AND METHOD FOR CALIBRATING EYE GAZE DATA

(71) Applicant: Mirametrix Inc., Westmount (CA)

(72) Inventors: Craig A. Hennessey, Vancouver (CA); Jacob Fiset, Montreal (CA); Nicholas Sullivan, Montreal (CA)

(73) Assignee: Mirametrix Inc., Montreal (CA)

( * ) Notice: Subject to any disclaimer, the term of this patent is extended or adjusted under 35 U.S.C. 154(b) by 0 days.

(21) Appl. No.: 14/263,636

(22) Filed: Apr. 28, 2014

(65) Prior Publication Data

US 2014/0320397 A1 Oct. 30, 2014

Related U.S. Application Data

(63) Continuation of application No. PCT/CA2012/050761, filed on Oct. 25, 2012.

(60) Provisional application No. 61/552,292, filed on Oct. 27, 2011.

(51) Int. Cl.

| | | |
|---|---|---|
| *G09G 5/00* | (2006.01) | |
| *G06F 3/01* | (2006.01) | |
| *A61B 3/113* | (2006.01) | |
| *G01S 3/78* | (2006.01) | |
| *G06K 9/00* | (2006.01) | |

(52) U.S. Cl.
CPC ............. *G06F 3/013* (2013.01); *A61B 3/113* (2013.01); *G01S 3/7803* (2013.01); *G06K 9/00604* (2013.01)

(58) Field of Classification Search
CPC ....... G06F 3/013; A61B 3/113; G01S 3/7803; G06K 9/00604
USPC ......................................................... 345/156
See application file for complete search history.

(56) References Cited

U.S. PATENT DOCUMENTS

| | | |
|---|---|---|
| 6,873,714 B2 | 3/2005 | Witt et al. |
| 7,657,062 B2 | 2/2010 | Pilu |
| 2007/0222947 A1 | 9/2007 | Kimata et al. |
| 2010/0295774 A1* | 11/2010 | Hennessey ................ 345/156 |
| 2012/0290401 A1* | 11/2012 | Neven .................. A61B 3/113 705/14.68 |

FOREIGN PATENT DOCUMENTS

| | | | |
|---|---|---|---|
| JP | 2010-029262 A | | 2/2010 |
| JP | 2010029262 A | * | 2/2010 |

OTHER PUBLICATIONS

Chen J. et al. "Probabilistic Gaze Estimation Without Active Personal Calibration"; IEEE Conference on Computer Vision and Pattern Recognition (CVPR); Jun. 20 to 25, 2011; pp. 609 to 616.
(Continued)

*Primary Examiner* — Mark Regn
(74) *Attorney, Agent, or Firm* — Blake, Cassels & Graydon LLP; Brett J. Slaney

(57) ABSTRACT

A system and method are provided for calibrating an eye gaze tracking system. The method comprises obtaining gaze data; obtaining at least one key point corresponding to a portion of media content being displayed; linking the gaze data to the at least one key point; and generating one or more calibration parameters by comparing gaze data with associated ones of the at least one key point.

24 Claims, 20 Drawing Sheets

(56) References Cited

OTHER PUBLICATIONS

Weaver et al.; "Gaze-Based Password Authentication through Automatic Clustering of Gaze Points"; IEEE Conferece on System Man and Cybernetics (SMC); Oct. 9 to 12, 2011 pp. 2749 to 2754.
Moreau, J.; International Search Report from corresponding PCT Application No. PCT/CA2012/050761; dated Jan. 9, 2014.

\* cited by examiner

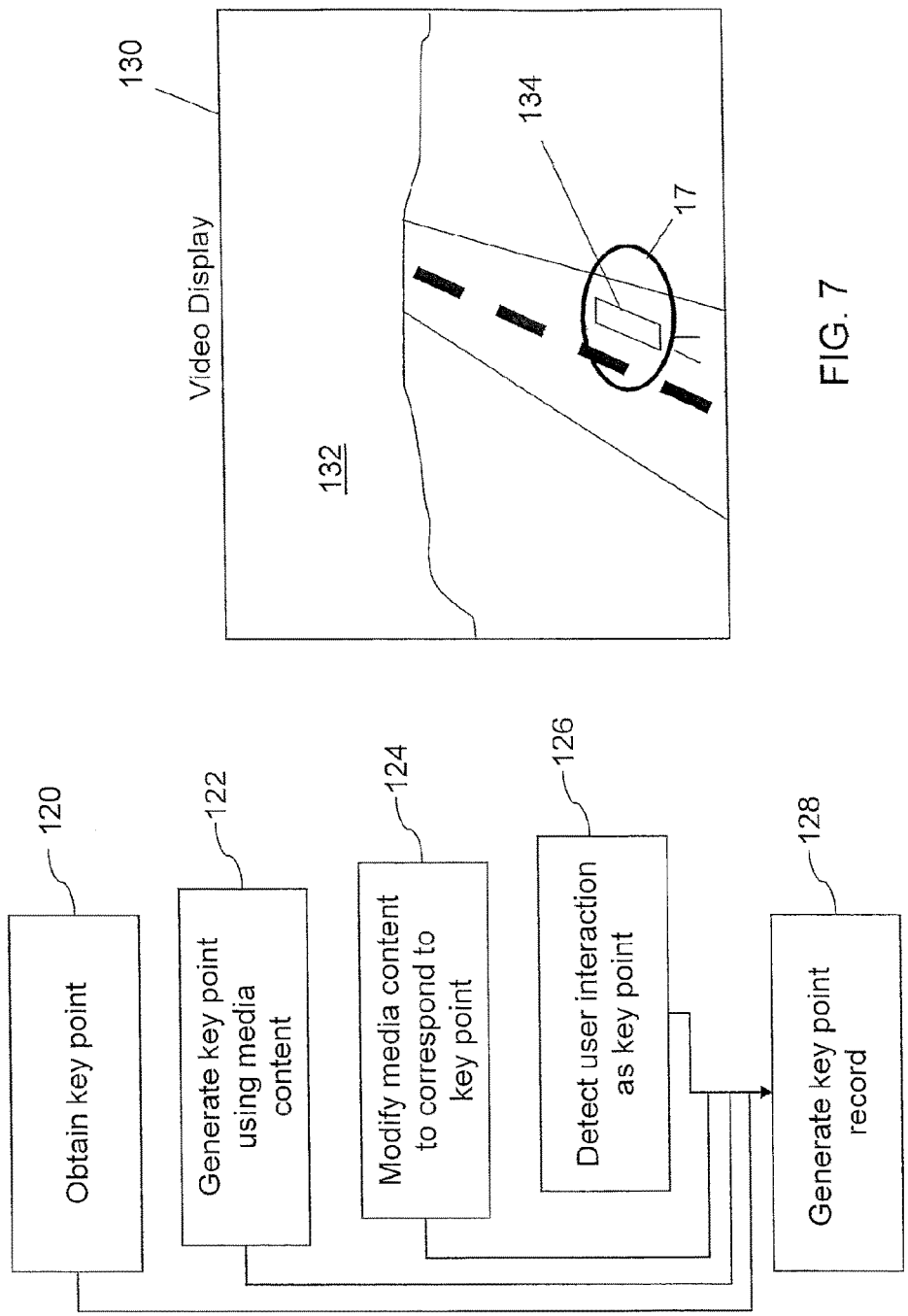

SYSTEM AND METHOD FOR CALIBRATING EYE GAZE DATA

CROSS-REFERENCE TO RELATED APPLICATIONS

This application is a continuation of International PCT Application No. PCT/CA2012/050761 filed on Oct. 25, 2012 which claims priority from U.S. Provisional Application No. 61/552,292 filed on Oct. 27, 2011, both incorporated herein by reference.

TECHNICAL FIELD

The following relates to systems and methods for calibrating eye gaze data.

DESCRIPTION OF THE RELATED ART

Eye tracking systems typically require calibration due to the anatomical structures of the eye that vary between subjects. Key parameters of interest to eye tracking include the offset between the optical axis (geometric mean) and visual-axis due to the position of the fovea on the retina, the curvature of the cornea, etc.

Calibrating an eye tracking system typically involves looking at known points displayed sequentially across a display screen, most often in a 3×3 grid or an X shaped pattern. While calibrating, the eye tracking system stores image information of interest, typically reflections off the cornea (glints) and the pupil position in the images of the face. Calibration data may also include computed parameters such as the position of the eyes and the line-of-sight for each eye.

Current calibration techniques can be completed quickly, often within 5 to 10 seconds. However, such a calibration requires the user to consciously participate in the calibration process by looking at the calibration positions. After calibration, the user may continue with their activity, such as watching a video, or browsing the Internet. If re-calibration is required for any reason, the user must stop their activity and repeat the calibration procedure.

It is an object of the following to address the above-noted disadvantages.

SUMMARY

It has been recognized that as eye tracking systems become increasingly used by the general population, there will be a need to simplify and/or reduce the calibration process, in particular the participation required by the subject. The following provides a system allowing calibration of eye gaze data with minimal to no conscious user interaction.

In one aspect, there is provided a method of calibrating an eye gaze tracking system, the method comprising: obtaining gaze data; obtaining at least one key point corresponding to a portion of media content being displayed; linking the gaze data to the at least one key point; and generating one or more calibration parameters by comparing gaze data with associated ones of the at least one key point.

In another aspect, there is provided a computer readable medium comprising computer executable instructions for performing the above method.

In yet another aspect, there is provided a system comprising a processor and memory, the memory storing computer executable instructions for performing the above method.

BRIEF DESCRIPTION OF THE DRAWINGS

Embodiments will now be described by way of example only with reference to the appended drawings wherein:

FIG. 6 is a flow chart illustrating an example set of operations that may be performed in generating a key point record.

FIG. 7 provides an example video display showing a scene including a rapidly moving object as a key point.

DETAILED DESCRIPTION

Figure 1:
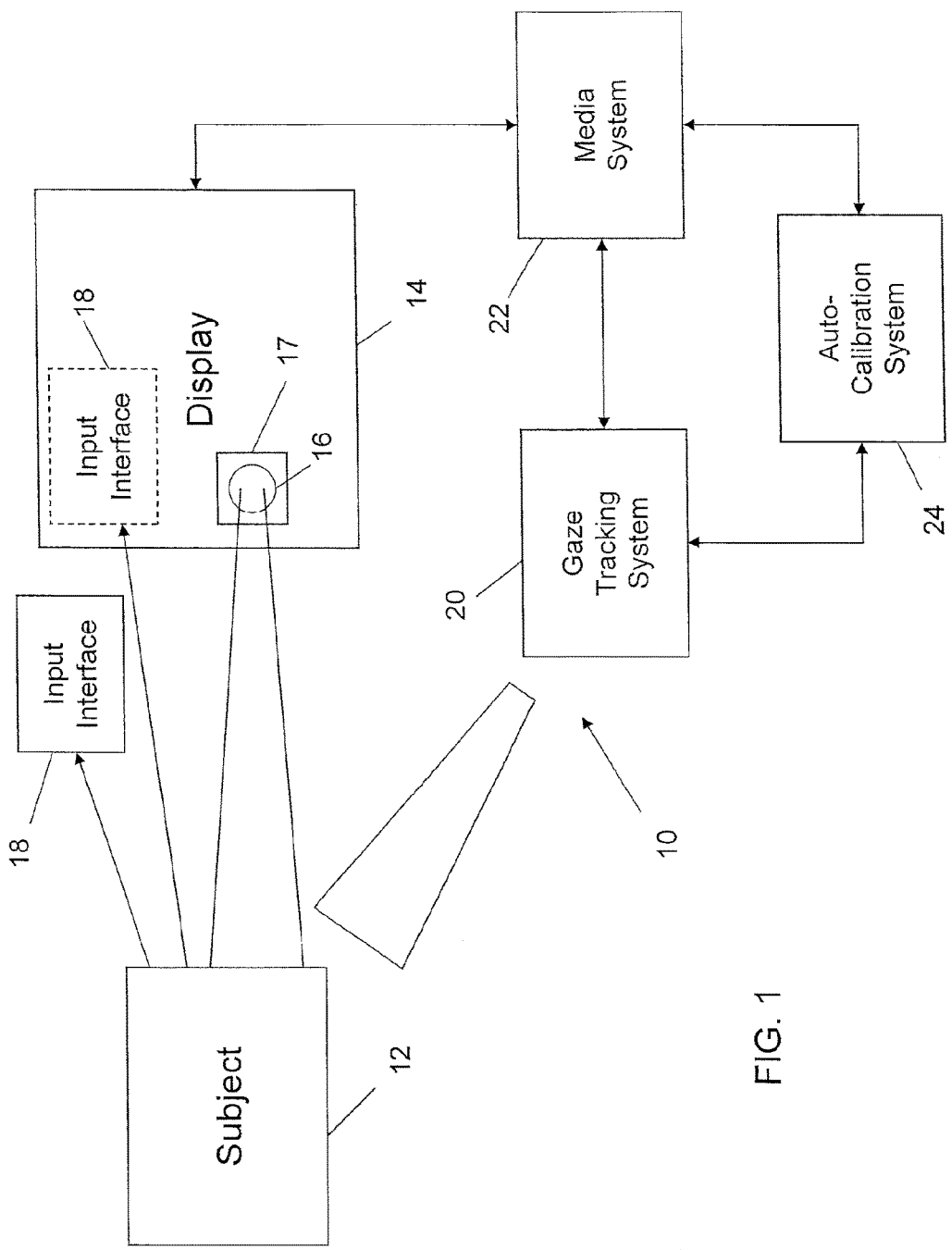
FIG. 1 is a block diagram showing an example of a subject viewing and/or interacting with a display and an auto-calibration system for calibrating eye gaze data obtained by a gaze tracking system.

It will be appreciated that for simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

The following provides a method for automating a gaze tracking system calibration based on display content and/or user actions that are likely to attract the subject's gaze. As discussed below, the following automatic calibration (auto-calibration hereinafter), also allows identification of an individual user based on a best fit of the individual to an entry in a database of eye-gaze calibrations.

Turning now to FIG. 1, an environment 10 is shown with which a subject 12 views or interacts with a display 14 in or provided by the environment 10. The environment 10 may be associated with a physical location such as an office, movie theatre, home theatre, etc.; or may represent components of one or more devices such as a television, smart phone, personal computer (PC), gaming console, tablet computer, etc. The display 14 may therefore be provided by or associated with any device capable of displaying media content to a subject (e.g., user, viewer, etc.). For example, the display 14 may represent a screen for a television (TV), computer monitor, mobile device, augmented or virtual-reality display, etc. and may provide a two dimensional (2D) or a three dimensional (3D) output.

In the example shown in FIG. 1, the subject 12 when viewing the display 14 has a direction of gaze, also known as a line of sight, which is the vector that is formed from the eye of the subject to a point on a object of interest on the display 14. The point of gaze (POG) 16 is the intersection point of the line of sight with the object of interest. The object of interest in this example corresponds to a virtual object displayed on the display 14. For 2D displays 14, the POG 16 lies on the surface of the display 14. For 3D displays 14, the POG 16 targets objects similarly to real-world objects, using the vergence of the eyes of the subject, or intersection of the line of sight from both the left and right eyes of the subject. The movement of the eyes can be classified into a number of different behaviors, however of most interest when tracking the POG 16, are typically fixations and saccades. A fixation is the relatively stable positioning of the eye, which occurs when the user is observing something of interest. A saccade is a large jump in eye position which occurs when the eye reorients itself to look towards a new object. Fixation filtering is a technique which can be used to analyze recorded gaze data and detects fixations and saccades. The movement of the subject's eyes and gaze information, POG 16 and other gaze-related data is tracked by a gaze tracking system 20.

Media content is provided on the display 14 for the subject 12 using a media system 22. In addition to displaying media content using the display 14, the media system 22 may be operable to provide a user interface (UI) in or with the environment 10 that includes one or more input mechanisms with which the subject 12 may interact. The subject 12 may interact with the environment 10 via an input interface 18. As shown in FIG. 1, the input interface may be external or peripheral to the display (e.g., keyboard, mouse, game controller, physical button, etc.) or may be incorporated into the display 14, e.g., wherein the display 14 is touch-sensitive and provides virtual button, links, and other input mechanisms that may be tapped, touched, swiped, etc.

An auto-calibration system 24 is also shown in FIG. 1, which interacts with the gaze tracking system 20 and a media system 22 to automatically calibrate the gaze tracking system 20. As will be explained in greater detail below, the auto-calibration system 24 uses key points 17 associated with, or inferred from, the media content displayed, rather than using strictly known calibration points with conscious participation by the subject 12. The key points 17 are locations of content (e.g., objects) that are more likely to catch the gaze of the subject 12.

Figure 2:
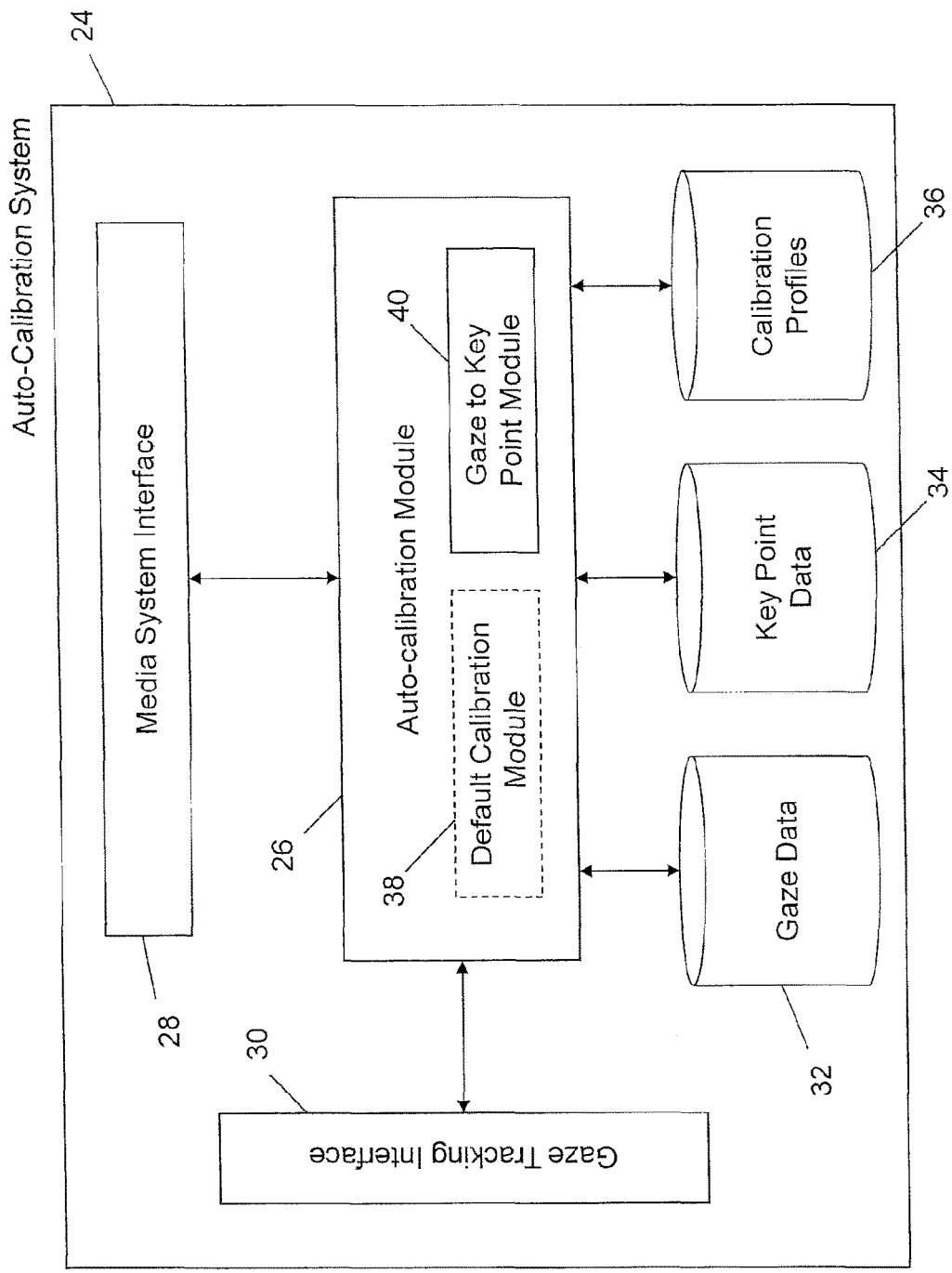
FIG. 2 is a block diagram illustrating further detail of the auto-calibration system shown in FIG. 1.

FIG. 2 illustrates an example of a configuration for the auto-calibration system 24. The auto-calibration system 24 includes an auto-calibration module 26 for automatically calibrating the gaze tracking system 20. The auto-calibration system 24 includes a media system interface 28 for communicating with or otherwise interacting with the media system 22. For example, the media system interface 28 may be used to determine key points 17 from media content and/or modify media content to include deliberate key points 17. The auto-calibration system 24 also includes a gaze tracking interface 30 for communicating with or otherwise interacting with the gaze tracking system 20. For example, the gaze tracking interface 30 may be used to obtain raw or pre-calibrated eye gaze data and/or provide calibration parameters to the gaze tracking system 20 for calibrating the POG 16 without conscious interaction by the subject 12.

The auto-calibration module 26 includes or otherwise has access to a gaze database 32 storing gaze data obtained from the gaze tracking system 20, e.g., via the gaze tracking interface 30; a key point database 34 storing key points 17 generated by the auto-calibration module 26, obtained from the media system 22, obtained from another external source (not shown), etc.; and a calibration profiles database 36 storing calibration profiles for at least one subject 12. It can be appreciated that the calibration profiles 36 may be associated with multiple subjects and thus the auto-calibration 24 may be operable to determine the subject 12 being tracked, whether or not multiple subjects 12 are being tracked, and to differentiate between subjects 12, e.g., to enable calibrations to be suited to particular subjects 12.

The auto-calibration module 26 may include a default calibration module 38 to be used in examples wherein the auto-calibration module 26 is operable to perform an initial calibration (e.g., default calibration) on raw POG data. It can be appreciated that the default calibration module 38 may also or instead be implemented by or reside in the gaze tracking system 20 or media system 22. In the example shown in FIG. 2, the auto-calibration module 26 also includes a gaze to key point module 40 for associating gaze data with key points 17 in the media content as will be explained in further detail below.

Figure 3:
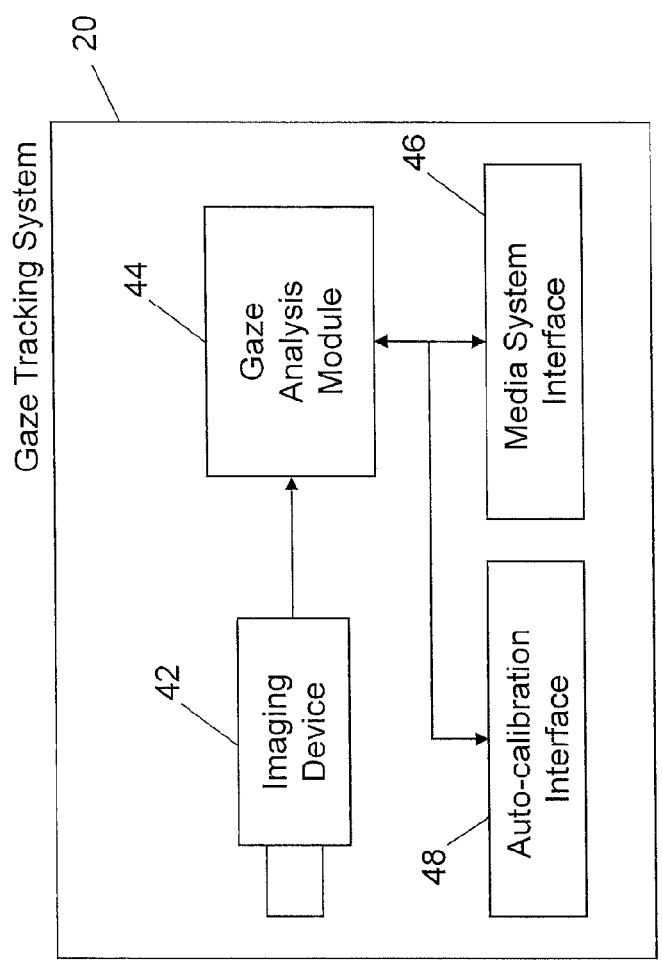
FIG. 3 is a block diagram of an example configuration for the gaze tracking system of FIG. 1.

An example of a configuration for the gaze tracking system 20 is shown in FIG. 3. The gaze tracking system 20 in this example includes an imaging device 42 for tracking the motion of the eyes of the subject 12; a gaze analysis module 44 for performing eye-tracking using data acquired by the imaging device 42; a media system interface 46 for interfacing with, obtaining data from, and providing data to, the media system 22; and an auto-calibration interface 48 for interfacing with, obtaining data from, and providing data to, the auto-calibration system 24. The gaze tracking system 20 may incorporate various types of eye-tracking techniques and equipment. An example of an eye-tracking system can be found in U.S. Pat. No. 4,950,069 to Hutchinson and entitled "Eye Movement Detector with Improved Calibration and Speed". It can be appreciated that any commercially available or custom generated eye-tracking or gaze-tracking system, module or component may be used. An eye tracker is used to track the movement of the eye, the direction of gaze, and ultimately the POG 16 of a subject 12. A variety of techniques are available for tracking eye movements, such as measuring signals from the muscles around the eyes, however the most common technique uses the imaging device 42 to capture images of the eyes and process the images to determine the gaze information.

Figure 4:
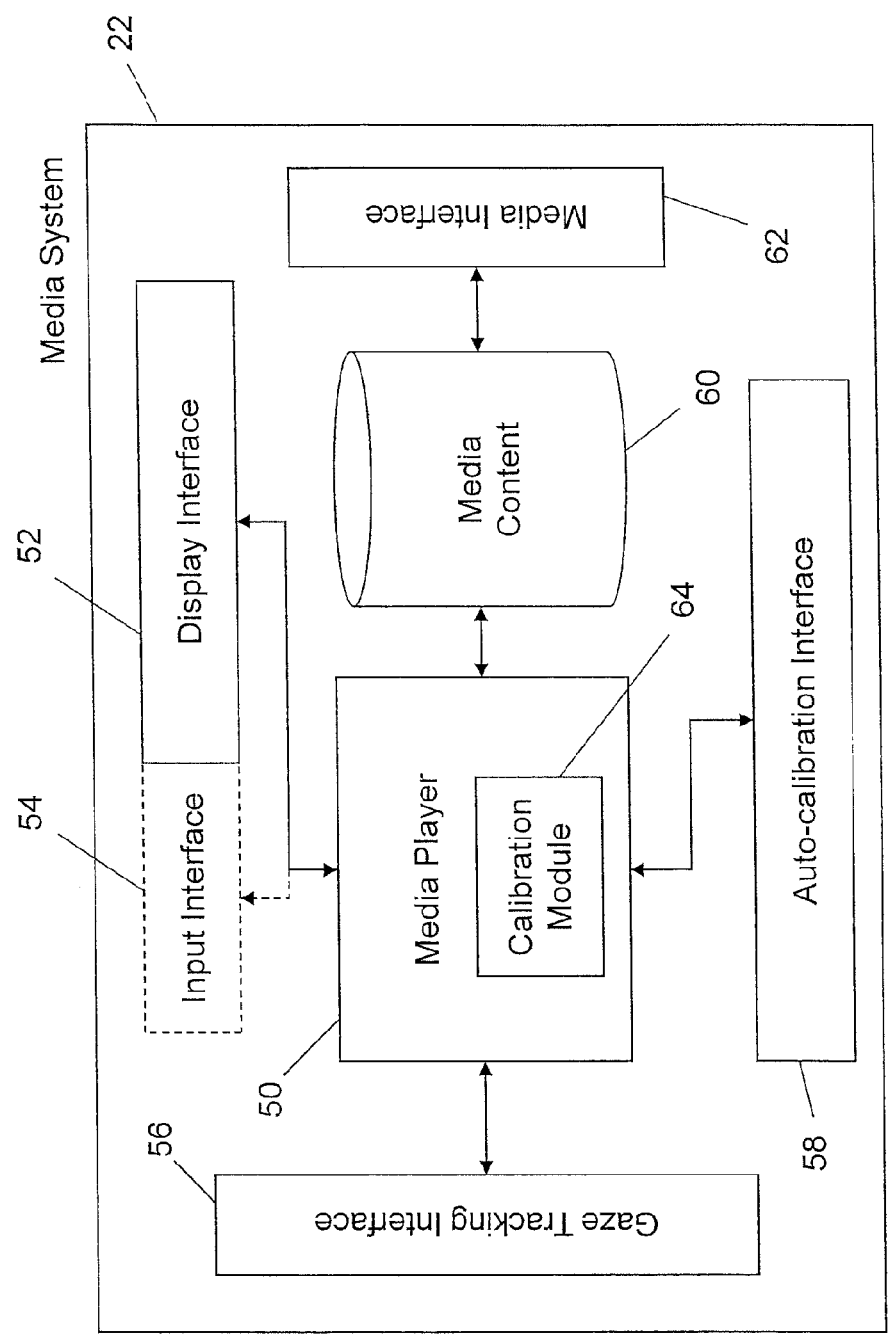
FIG. 4 is a block diagram of an example configuration for the media system shown in FIG. 1.

An example of a configuration for the media system 22 is shown in FIG. 4. The media system 22 in this example includes a media player 50 which may generally represent any module, component, or application that is operable to generate, render, or otherwise provide media content to or on the display 14 via a display interface 52. The media system 22 may also include an input interface 54 for detecting user interactions, e.g., a mouse click or tap on a touchscreen, etc. The media system 22 also includes a gaze tracking interface 56 for interfacing with, obtaining data from, and providing data to, the gaze tracking system 20. The media system 22 also includes an auto-calibration interface 58 for interfacing with, obtaining data from, and providing data to, the auto-calibration system 24. The media player 50 includes or otherwise has access to a media content database 60, which may be used to store media content, either persistently or temporarily (e.g. by providing a data cache). Media content may be provided to and stored in the media system 22 via a media interface 62, e.g., via USB, Ethernet, Bluetooth, network drive, DVD, etc. It can be appreciated that the media content may be loaded on and played by the media system 22, or may be streamed to or by the media system 22.

Figure 5:
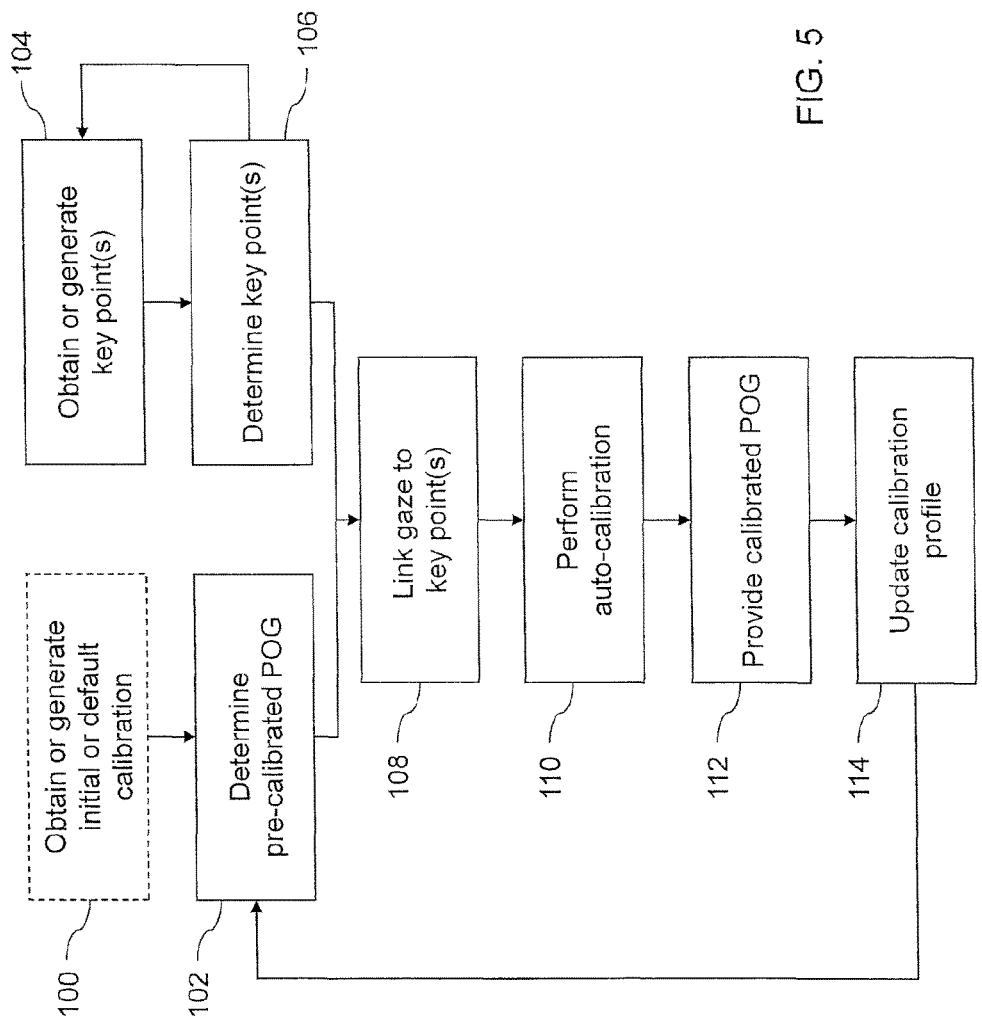
FIG. 5 is a flow chart illustrating an example set of operations that may be performed in calibrating point of gaze (POG) data.

FIG. 5 illustrates an example set of computer executable operations that may be performed, e.g., by the auto-calibration module 46, in utilizing gaze data (such as POG 16) and key points 17, to automatically calibrate the gaze tracking system 20. While it is possible to perform the auto-calibration technique described herein on raw eye gaze data provided by the gaze tracking system 20, as shown in dashed lines at 100, it may be beneficial to apply an initial or default calibration which is then refined in the auto-calibration procedure. As shown in FIG. 5, the initial or default calibration may be generated by the auto-calibration module 46, e.g., using the default calibration module 38, or may be obtained from the gaze tracking system 20. In other words, any pre-calibration, default calibration, or initial calibration may be performed by the gaze tracking system 20 and provided to the auto-calibration system 24, or may be performed by the auto-calibration system 24 on raw eye gaze data provided by the gaze tracking system 20.

The initial or default calibration maybe be a single generic profile, a last known calibrated profile (from a previous session), or multiple profiles such as a set of family profiles, or set of generic profiles based on human features such as gender or age. In the event of multiple default profiles, the automatic calibration algorithm described herein may test each profile in turn for a best fit to the initial image feature key points at the start of the automatic calibration procedure. Additional information may be used to assist in selecting the initial or default profile, such as facial recognition, or other biometric measures such as the subjects size, height, skin color, eye color, etc.

A pre-calibrated POG 16 is be provided at 102, which may include raw POG data or data that has been subjected to an initial or default calibration as discussed above. It may be noted that key points 17 can be provided in the media content over time, throughout various user activities, for example, as the subject 12 watches or interacts with the display 14. At each key point 17 stored in the key point database 34, the image data (i.e. a location in the image on the display 14 the key point 17 is located) and the eye gaze data such as POG 16 are stored in the gaze database 32, along with the estimated POG 16, based on either the initial or default calibration profile performed at 100, or the automatic calibration profile as the system operates. It can be appreciated that the initial or default calibration at 100 typically occurs only at startup or when calibration parameters from an auto-calibration have not yet been obtained.

The key points 17 refer to locations in the media content that include content that is more likely to attract the gaze of the subject 12, such as faces (and eyes, mouth, etc), areas of fast motion, higher brightness, flashing or a change in brightness, on screen logos or user interface elements, and user actions such as mouse clicks, etc. In the case of touch displays, key points 17 may be from locations on the display where the viewer's press with their finger. The location of the key points 17 may be encoded beforehand or automatically detected in the content being displayed using techniques such as facial recognition, motion tracking, brightness analysis, operating system feedback, etc. Content that may be analyzed can include videos such as TV shows and movies, computer programs, operating system interfaces, web pages, etc. It can be appreciated that if control of the media content is possible, small graphical overlay elements or changes in image intensity may provide another mechanism for attracting the viewer's gaze to desirable positions, such as regions with a low density of native key points 17. Similarly, an introductory video created with logos and objects that could attract the user's attention can be used. By placing said objects in key positions one after another, they can be used as key points.

Therefore, the key points 17 may be pre-associated with media content or generated "on-the-fly". The auto-calibration module 26 obtains or generates one or more key points 17 at 104 and determines the key points 17 at 106. The key points 17 may then be linked at 108 to the gaze data obtained at 102. The auto-calibration module 26 may then perform the auto-calibration procedure at 110. The calibrated POG 16 may then be provided at 112 to be used for a variety of interaction and analytics techniques. Interaction techniques may include eye typing, gaze based control of on-screen user interfaces, sharing of context from gaze, etc. examples of which may be found in co-owned U.S. Provisional Patent Application No. 61/413,964, filed on Nov. 15, 2010, and entitled "Method and System for Media Display Interaction Based on Eye Gaze Tracking", the contents of which are incorporated herein by reference. Analytics techniques include analyzing viewer behavior patterns, such as interest in on-screen product placements, pop-up advertisements, content navigation, etc. Examples of such analytics techniques may be found in U.S. Application No. 61/413,964 noted above, and additionally in U.S. application Ser. No. 12/727,284 filed on Mar. 19, 2010, published as U.S. Publication No. 2010/0295774, and entitled "Method for Automatic Mapping of Eye Tracker Data to Hypermedia Content", the contents of which are also incorporated herein by reference. The calibration profile for the subject 12 may then be updated at 114.

It can be appreciated that since the auto-calibration procedure may be performed periodically or continuously as the subject 12 views or interacts with the display 14, the process may be repeated at 102 with the updated calibration profile being used instead of an initial or default or previously calibrated set of parameters. Similarly, it can be appreciated from FIG. 5 that key points 17 may be obtained periodically or continuously throughout the subject's interactions with or viewing of the media content and thus may continue to populate a key point 17 list for subsequent calibrations.

FIG. 6 illustrates an example set of computer executable operations that may be performed in obtaining or generating key points 17. As can be appreciated from FIG. 6, the key points 17 can be generated or obtained in various ways. For example, a key point 17 or indication thereof may be obtained at 120, e.g., from previous manual creation and storage for future use in the media system 22. A key point 17 or indication thereof may also be generated from the media content at 122, e.g., by the media system 22 or the auto-calibration system 24. Existing media content may also be modified, either prior to use or on-the-fly to create an artificial or exaggerated key point 17 at 124. For example, as noted above, brightness or speed of an object can be controlled in an attempt to increase the likelihood that the subject 12 will view the key point 17. The auto-calibration module 26 may also rely on detection of a user interaction at 126 to determine a key point 17 that can be associated with gaze data. For example, the subject 12 may be more likely to be gazing at an icon on a display 14 that has been just selected. A key point record may then be generated at 128.

It can be appreciated that key points 17 may be 2D points such as the position of a mouse click, or polygonal regions such as rectangles, wherein the center of the area may be used as the key point location. A typical rectangular key point record with key point ID number (or name), timestamp, position (X, Y as % of screen) and size (width, height) may be structured as shown in Table 1 below.

TABLE 1

Example Key Point Record

| ID | Timestamp | X | Y | Width | Height |
|---|---|---|---|---|---|
| 1 | 12:44:23.123 | 0.52 | 0.56 | 0.12 | 0.12 |

Viewing behavior may also present options for determining key points 17 in display content. For example, when watching a letterboxed movie, it may be unlikely that the POG 16 strays from the letterbox boundary. In another example, when a subject 12 reads content on a display 14, the POG 16 typically exhibits a saw tooth pattern, wherein the start and end of a line may provide key point locations. When viewing web pages, the document object model (DOM) provides information into the position of content on the display 14 such as text for reading, and regions with embedded videos which are likely to attract the eyes. For content with a generally consistent on screen patterns (such as the Windows® "Start" button on the lower left of the display, or the Apple® "Dock" at the lower part of the display), or TV content which is primarily focused in the central part of the display, previously recorded data from other users may be used to predict the location of key points as described further below.

Automatic calibration may be used with both 2D and 3D point of gaze estimation algorithms. For 2D scenarios, the calibration uses 2D (X,Y) key points 17. For 3D scenarios, the calibration uses 3D (X,Y,Z) key points 17. For 2D point of gaze algorithms, the calibration may include fitting coefficients to $n^{th}$ order polynomials which map image features to screen coordinates. For 3D point of gaze algorithms, the calibration may attempt to parametrically identify the offset between the optical axis and visual axis of the viewer. When a 3D gaze tracking system 20 is being used on a 2D display 14, the depth of the display 14 provides an additional constraint for identifying key points.

Various example key points 17 are shown in FIGS. 7-10.

In FIG. 7, a video display 130 is shown that includes a scene 132 in which a vehicle 134 is rapidly moving along a roadway. The vehicle 134 may serve as a key point 17 in this example since the rapidity of its movement is more likely to catch the gaze of the subject 12 than the background of the scene 132. In the example shown, the object of interest is moving across the screen, and therefore the key point position also moves accordingly.

Figure 8:
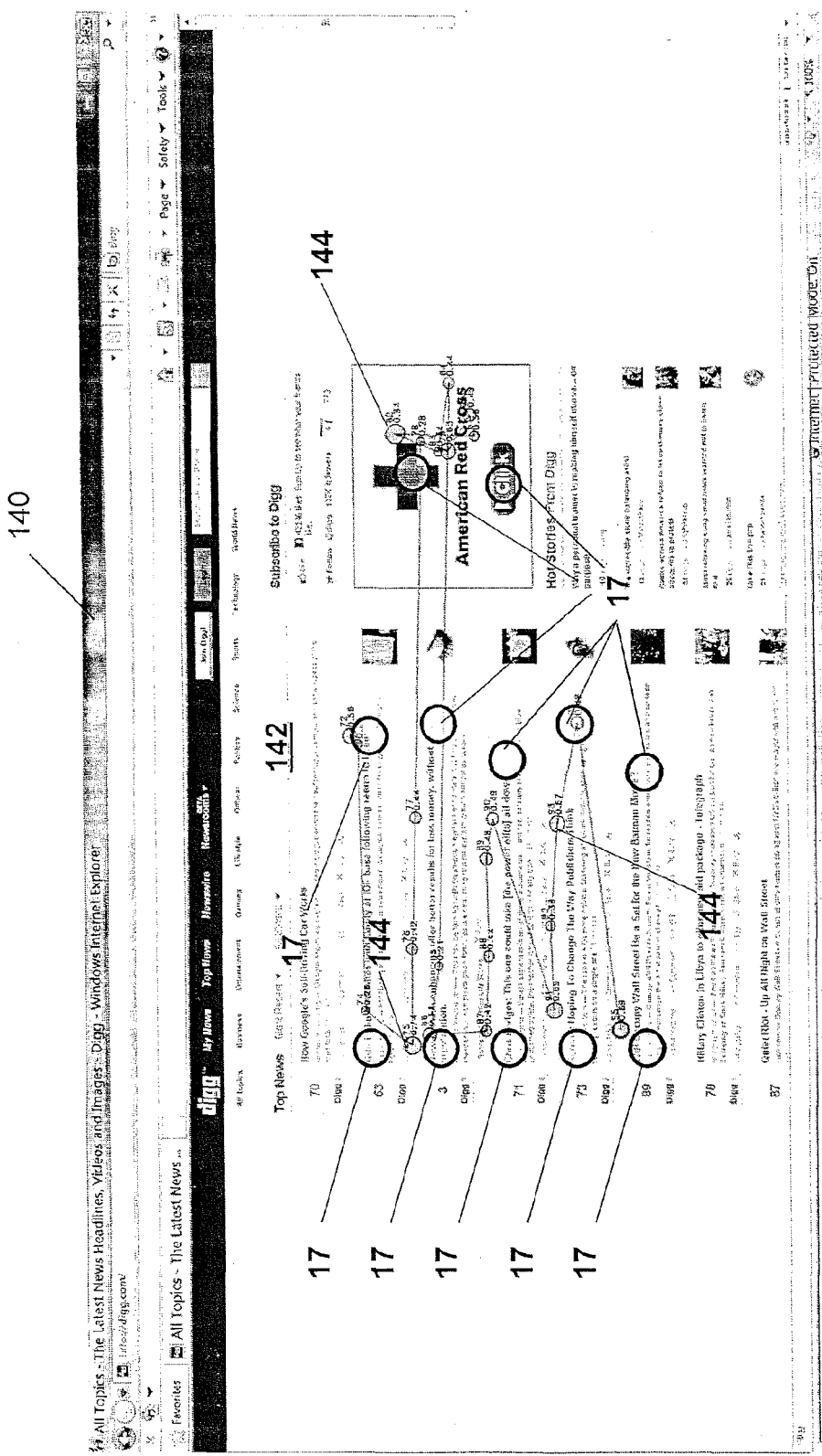
FIG. 8 is a screen shot of an example web browser showing web content including multiple key points and detected fixations.

In FIG. 8, numerous key points 17 are identified on web browser UI 140 displaying a web page 140. The key points 17 illustrate expected reading behavior that may be mapped to detected fixations 144 on the display 14.

Figure 9:
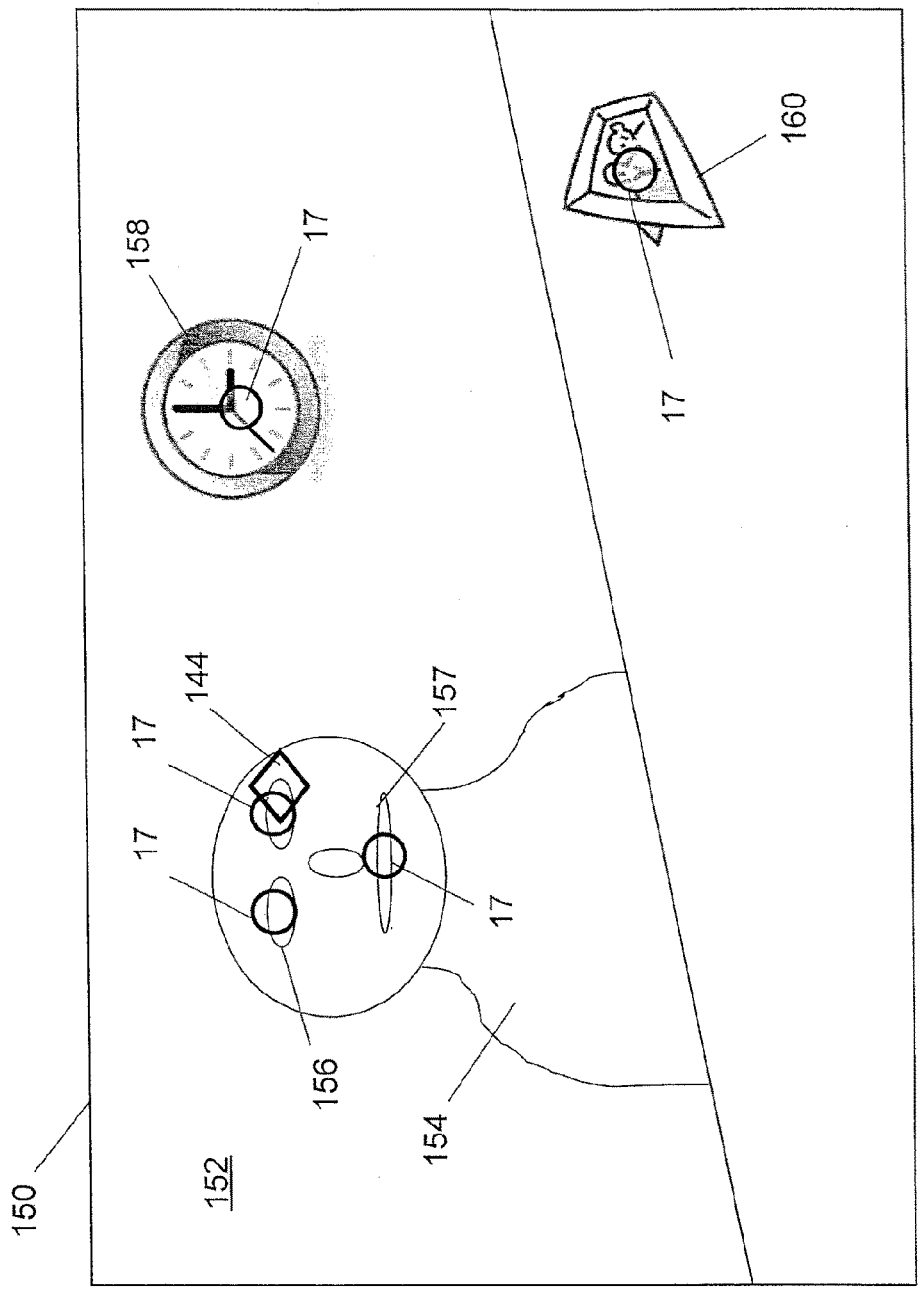
FIG. 9 provides an example of a still frame from video content that includes multiple key points and detected fixations.

In FIG. 9, an example television or movie scene 152 is displayed on a video display 150 in which a character 154 is participating in a dialog. In the scene 152 being shown, a clock 158 and a picture frame 160 may correspond to potential key points 17, in addition to facial features such as the character's eyes 156 and mouth 157. A fixation 144 is shown with a diamond in FIG. 9. It may be noted that there may be any number of key points 17 (or none at all) at any point in time, while there is only one point of gaze 144 for each viewer at any point in time. As will be discussed subsequently, the key points 17 nearest to the point of gaze 144 will be used in the auto-calibration algorithm.

Figure 10:
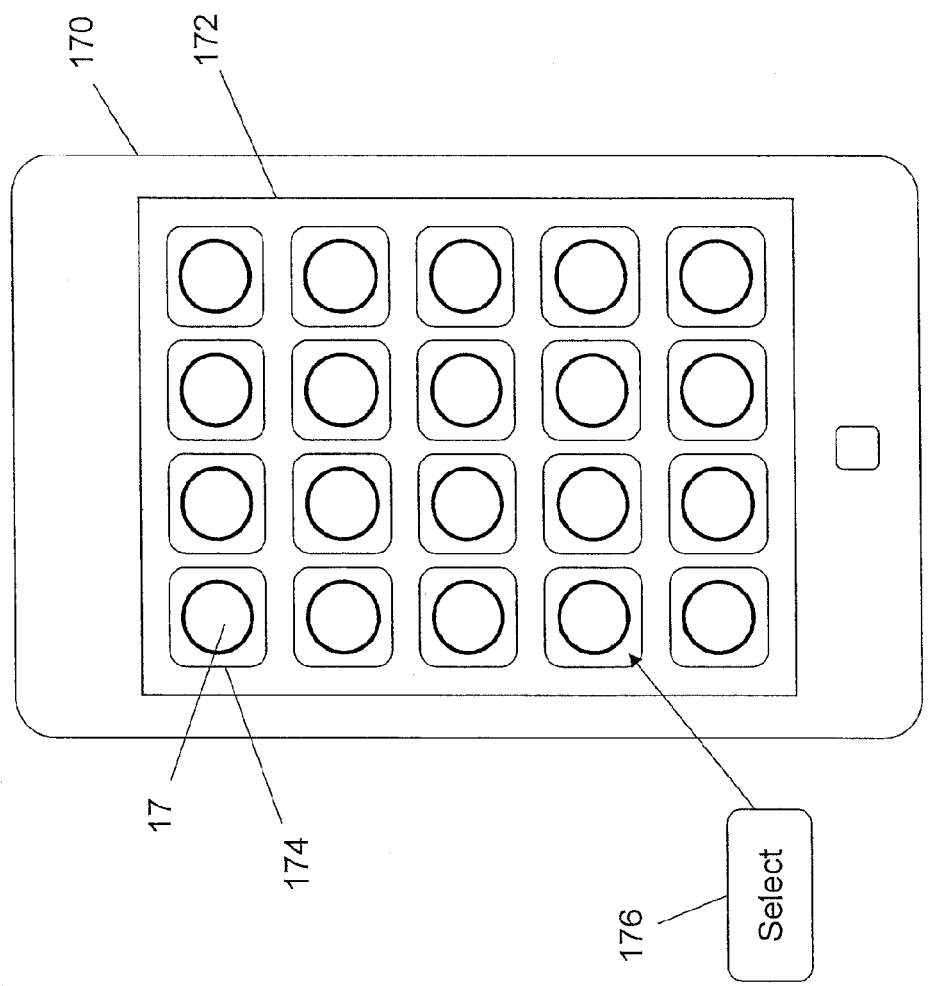
FIG. 10 is a pictorial view of a smart phone displaying a number of icons which are used as key points.

As described above, in addition to key points 17 from videos, key points 17 on a display 172 of a handheld or portable device such as a smart phone 170 may correspond to user interface elements 174, such as the grid of app icons as shown in FIG. 10. The use of touch interface with displays adds to the potential sources of key points 17. The touch input location 176 typically corresponds to where a user is looking, in order to guide the finger to the correct position on the display 172, which makes for a particularly good key point 17.

Figures 11, 12:
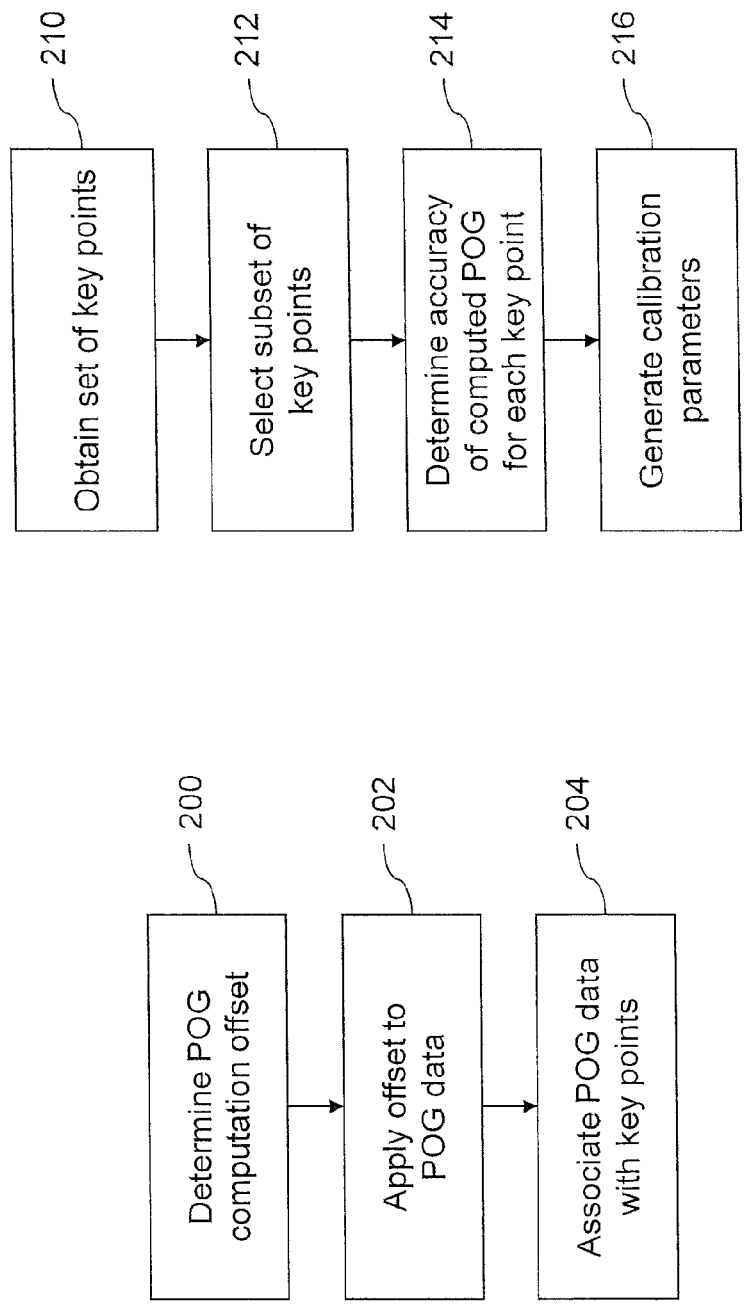
FIG. 11 is a flow chart illustrating an example set of operations that may be performed in linking POG data to key points.
FIG. 12 is a flow chart illustrating an example set of operations that may be performed in an auto-calibration method.

When linking gaze data to key points 17 at 108 (referring back to FIG. 5), it may be noted that the gaze tracking data may exhibit a time lag between when the subject 12 was viewing a key point 17, and the eventual computed POG 16. This time lag may be due to the time required to capture and transmit an image, process the image, compute the POG, or another other processing step. As shown in FIG. 11, to compensate for this lag, a time offset to the POG timestamp may be generated at 200, applied or added at 202 to better align the POG 16 with the content that was displayed, and the time shifted POG 16 associated with a key point 17 in the media content at 204. For example, if the subject 12 gazed at a face on the display 14 at time T=10 seconds, and it takes 25 ms to compute the POG 16, resulting in a POG timestamp of T=10.025 s, then a time shift of −0.025 seconds would be added to all POG estimates.

Referring now to FIG. 12, a sequence of key points 17 in time may be obtained for the auto-calibration procedure performed at 110 (referring back to FIG. 5) at 210, with the resulting calibration evaluated on a subset of key points 17 selected at 212, which are then used as test points. The test points are used at 214 to test the accuracy of the estimated POGs 16. Accuracy may be determined as measured by the Euclidean distance between the estimated POG 16 and the test key point 17 and the determined accuracy used to generate calibration parameters at 216. Calibration parameters (used to form the calibration profile) may include the constants for $n^{th}$ polynomial mapping between image features and the POG, as well as the horizontal and vertical angular offsets required to rotate the optical axis into the visual axis.

It can be appreciated that some of the key points 17 may be invalid, since a subject 12 may not necessarily be looking at every key point 17. Therefore, a key point may be used if the distance between the POG and any key point (Euclidean error) is lower than a certain threshold, or a random selection of key points 17 can be used in the calibration and evaluation procedures, and the process iterated until the most accurate result is achieved. For example, if there are ten key points 17 in the database 34 to be used for performing the calibration ($K_i$, i=1 . . . 10), and ten key points are available for evaluation ($E_i$, i=1 . . . 10), one iteration may use $K_1$, $K_5$, $K_6$, $K_8$, $K_9$, and $E_3$, $E_4$, $E_5$, $E_7$, $E_{10}$. Another set may be $K_2$, $K_3$, $K_4$, $K_8$, $K_9$, and $E_1$, $E_2$, $E_3$, $E_7$, $E_{10}$. The resulting calibration profile of whichever set resulted in the highest accuracy may then be used for subsequent POG estimation.

An additional method of rejecting/accepting key points for a particular user based on its validity could involve taking advantage of additional knowledge of the content type. For example, with film/TV content, most of the gaze is focused on the center of the image, with particular events occurring at extremes that draw the attention of the user (such as sports scores or animated network logos). One can use the center of the display to calculate the direction of the key point from the center, and reject key points as invalid when the user's gaze does not also move in a similar direction (e.g., even if the uncalibrated gaze point is close to the key point). For example, if the on screen key point appears in the top right of the display, and the uncalibrated gaze position is found to the lower left (with respect to the center or average of the uncalibrated gaze points) then the key point is unlikely to be correlated with that gaze position estimate. After this, a similar method to the above method for cycling through calibration points can be used, with spatial constraints added. As opposed to cycling through every possible combination of key points, one can separate the points into bins based on their spatial location and order each bin based on some additional criteria (such as its approximation to the center of the spatial window). This would decrease the search space considerably.

Figure 13:
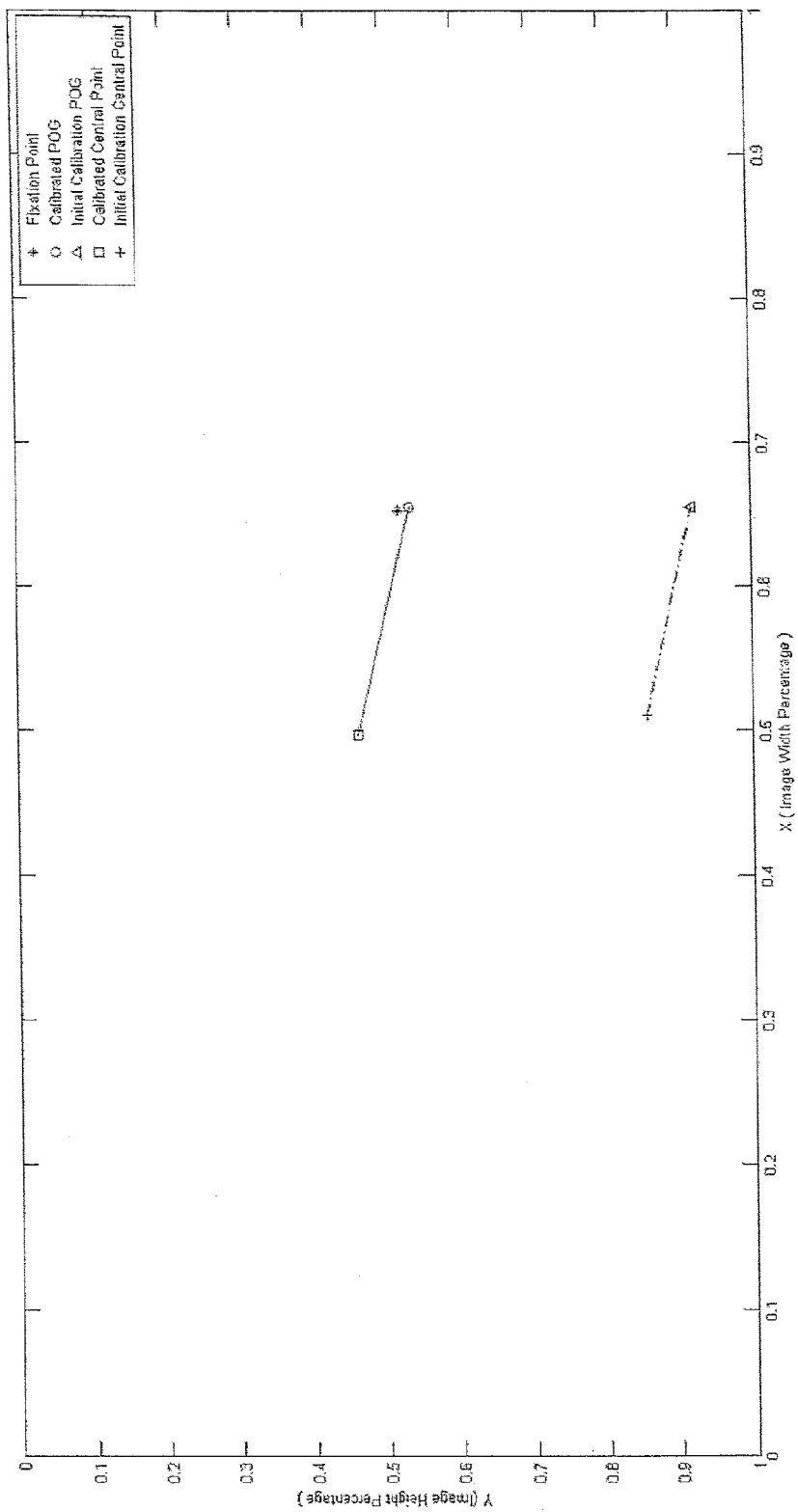
FIG. 13 is a graph of POG estimates in a video using both a manual calibration and an initial calibration.

In FIG. 13, a sample video frame's central point and key point for both a user's manually calibrated POGs and the initial calibration POGs are shown. As can be seen in FIG. 13, the vector from the key point to the central point can be used to determine the direction of the key point. This, in turn, can help determine if a user is viewing a particular key point or not, aiding in filtering invalid points for calibration.

Since the calibration procedure does not require conscious user participation, it may be run at any point during the subject's activity. The calibration may also be performed continuously, wherein the oldest key points 17, or key points 17 located in regions of the display 14 with a high density, are removed from the calibration point list, and the new calibration points added. Key points 17 in high density locations may also be weighted less highly than key points 17 from lesser viewed regions of the display 14 such as the corners. For example, if $K_1$, $K_5$, $K_6$, $K_8$, $K_9$, are currently used for creation of the calibration profile, and the addition of $K_{11}$ and/or the removal of $K_1$ improves the overall calibration profile accuracy then the new set of calibration key points 17 are retained, otherwise the previous profile is maintained.

Figure 14:
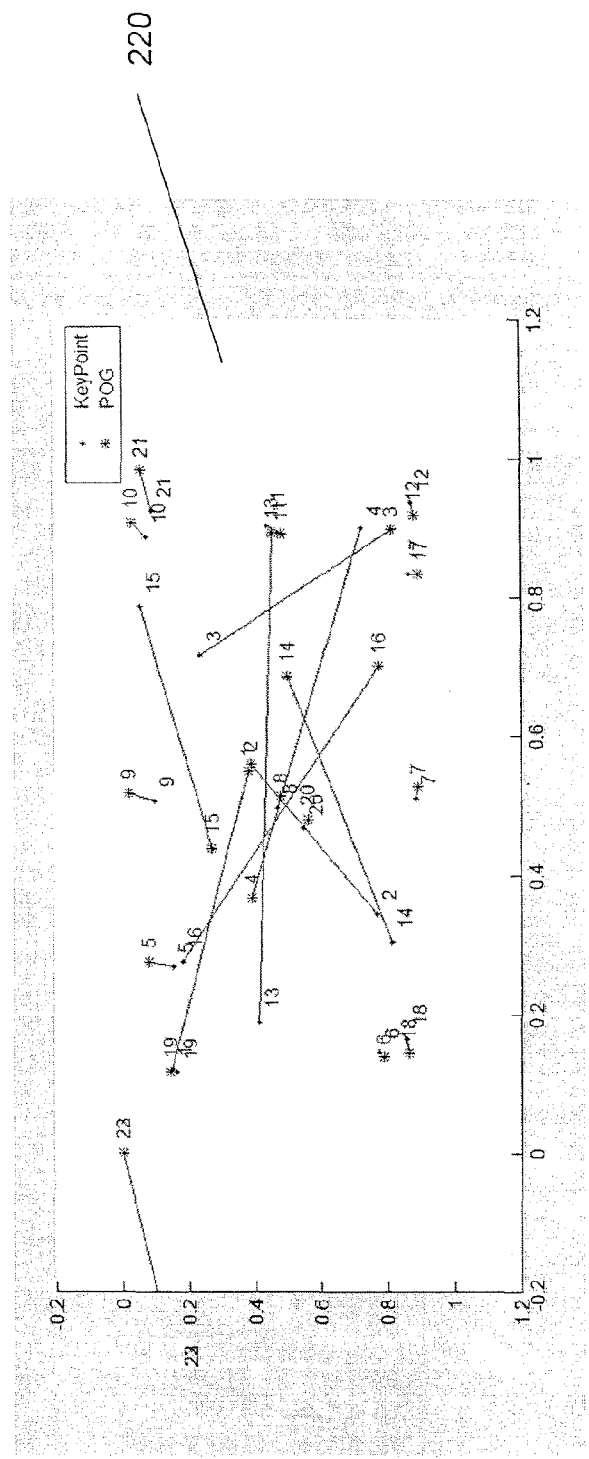
FIG. 14 provides a chart corresponding to an example sequence of key points and associated POG estimates.

FIG. 14 is an illustration of a labeled sequence of key points 17 with a corresponding labeled sequence of POG estimates. In the example chart shown, a sequence of key points 17 and a sequence of corresponding POG 16 estimates (recorded at the same time as the key point) are shown labeled from 1 to 23 on a display screen with normalized width and height (0,0 is top left and 1,1 is bottom right). In this example a default calibration profile has been used to estimate the POG 16.

Figure 15:
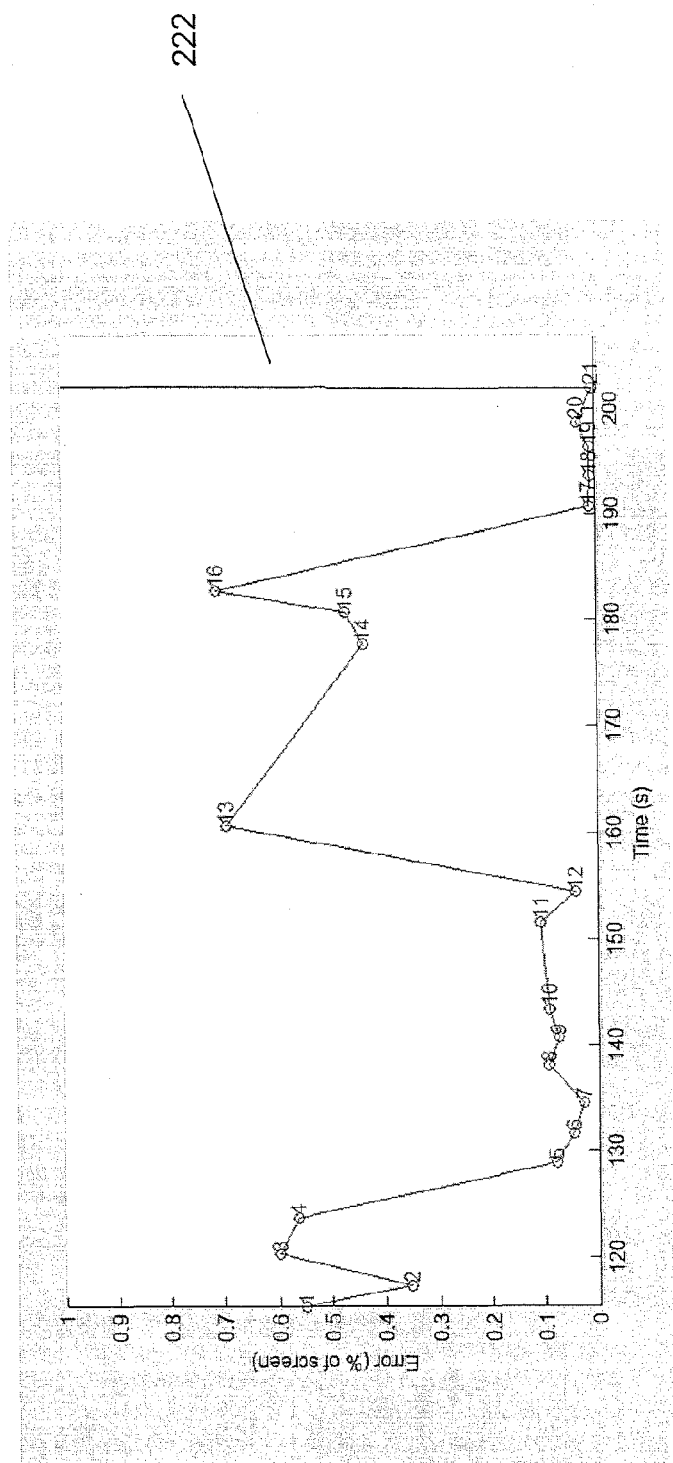
FIG. 15 provides a chart corresponding to an example of error estimates based on the key points and POG estimates shown in FIG. 14.

FIG. 15 shows the resulting error between key point and POG. If an error threshold for a valid key point 17 is set to some percentage of the screen (for example 10%), the key points 17 from 1 to 5 will not match with the point of gaze estimates, i.e. the subject 12 was not looking at those particular key points 17, based on a default calibration profile. The key points 17 from 5 to 12 however are below the threshold and therefore used to improve the calibration profile. The key points 17 numbered 13 to 16 are invalid, while the key points 17 numbered from 17 to 21 are below the threshold again and are valid.

Figure 16:
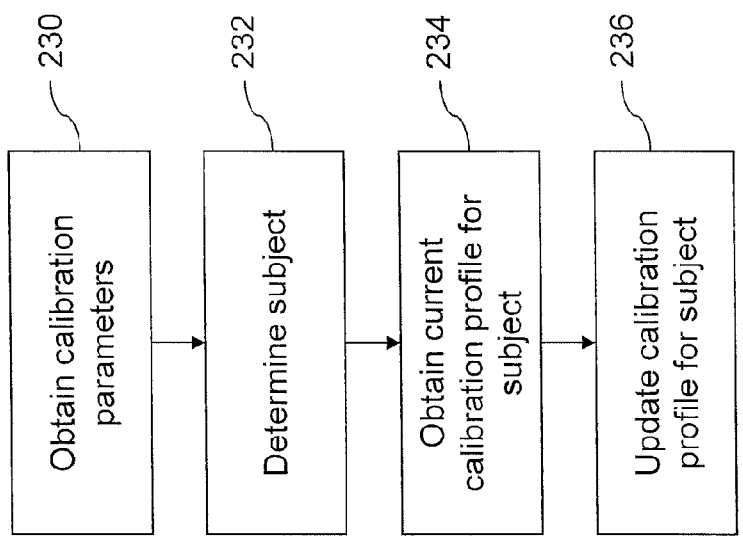
FIG. 16 is a flow chart illustrating an example set of operations that may be performed in updating a calibration profile.

It can be appreciated that in the event that more than one subject 12 are being observed by the gaze tracking system 20, either sequentially or at the same time, the calibration profiles may be stored independently for each user. After a number of subjects 12 have been calibrated, individual viewers (for example, mom/dad/children) can be automatically identified by matching the performance of each calibration in the calibration profiles database 36 with the subject 12, and a set of current key points 17 to be used as test points. FIG. 16 illustrates an example set of operations that may be performed at 114 (referring also back to FIG. 5) in updating a calibration profile. At 230, the calibration parameters generated during the auto-calibration procedure are obtained and the auto-calibration module 26 determines the subject 12 at 232. As noted above, different subjects 12 may be tracked either at the same time or at different times and thus the calibration profile corresponding to the subject 12 associated with the calibration is to be updated. The current calibration profile for the subject 12 is obtained at 234 from the calibration profiles database 36 and the obtained calibration profile for that subject is updated at 236. The updated calibration profile includes the new constants for the polynomials that map image features to the POG, or angular offsets for rotating the optical axis into the visual axis. The calibration profile may also include information on other biometric measurements such as viewer height, size, age, gender, etc.

Figure 17:
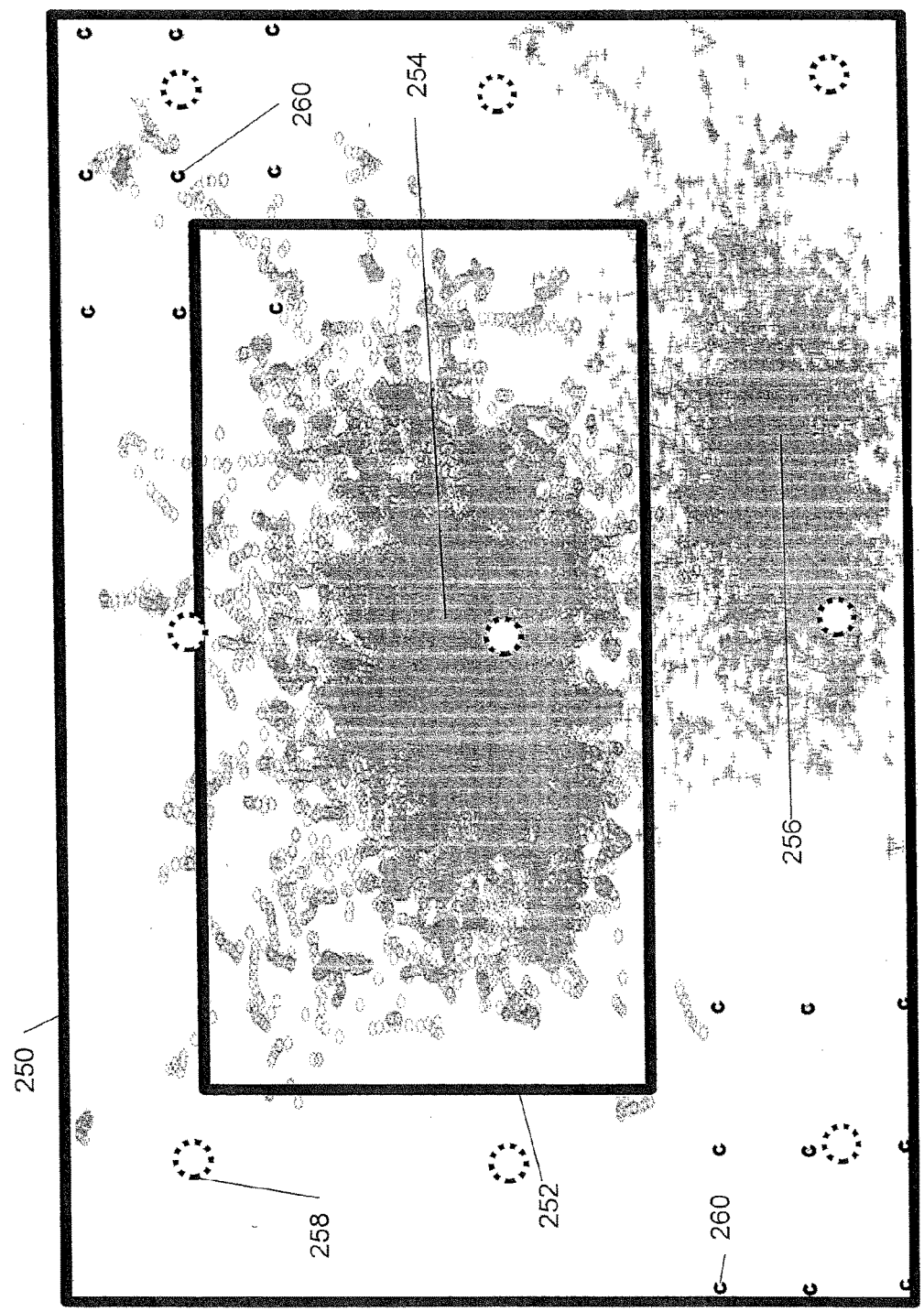
FIG. 17 illustrates an auto-calibration method using a statistical approach of a known situation.

FIG. 17 illustrates elements that may be used to perform an automatic calibration using a statistical approach. A screen 250 where, for example, TV content is displayed is shown, and the box 252 is a representation of a "high gaze region" typical of TV shows and movies. A well calibrated cloud of data 254 is also shown and illustrates what the system described herein can achieve. An intermediate cloud of data 256 is also shown, which may be the result of a test in an iterative process. The larger points 258 may be used for the first iteration of the calibration process, and the relatively smaller points 260 can be used for the second iteration in the auto calibration process.

Figure 18:
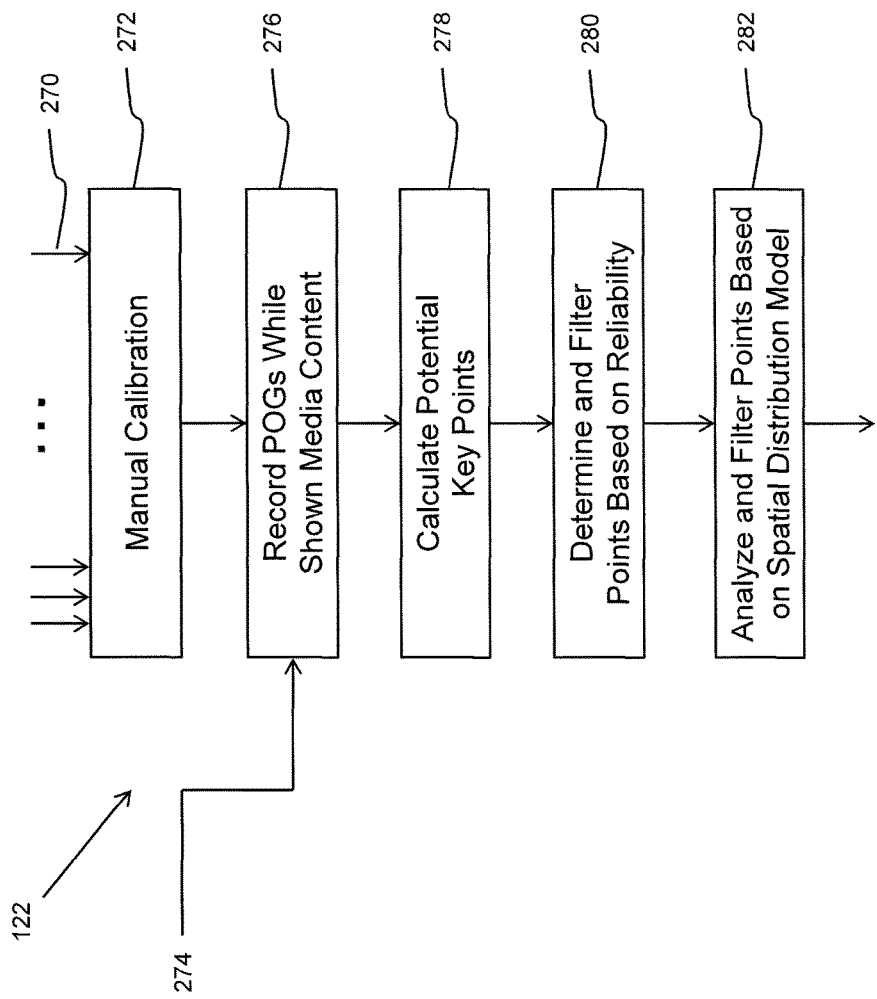
FIG. 18 is a flow chart illustrating an example flow graph to determine key points from a given set of media content.

FIG. 18 illustrates an example set of operations that may be executed in performing the calculations of block 122 in FIG. 6. In the operations shown in FIG. 18, key points 17 are obtained from media content using previous knowledge of how other users viewed the media. For a particular video, user gaze inputs 270 are calibrated using a calibration method at 272 (e.g., manual as illustrated or otherwise). The inputs 270 are then provided with media content 274 to view, and the POGs are stored at 276. This data is then analyzed per a discrete instance of time at 278, using the multiple users to calculate the average and standard deviation of the fixation points at any one point in time. Subsequently, the reliability of these fixation points is determined, and the most reliable points are kept at 280. Reliability can be measured by the degree of similarity between gaze estimates of the group of users (the lower the standard deviation or variance the better). Particularly, local minima under certain thresholds may be accepted as a key point 17. The maintained key points 17 are analyzed for spatial distribution at 282, and key points 17 are removed or kept to maximize their distribution across a spatial region of the display. This is performed in order to ensure the output key points are spatially distributed evenly, as having points biased towards one spatial region could lower the accuracy of calibration.

The operations shown in FIG. 18 can additionally be used by content providers to ensure manual calibration is unnecessary. By creating an introductory video (such as a corporate welcome animation) in which known content locations and saliency are shown, a short calibration video imperceptible to the user may be viewed. A content provider may then pre-append this introductory video to all of its standard content. Future users are calibrated using the introductory video and their fixation points are subsequently stored while watching the content. Once a set number of users have viewed a piece of content, it too can be analyzed via the previously described operations and used as an automated calibration video. Once enough media content has been analyzed, the content provider may choose to minimize/remove the introductory video and rely solely on the analyzed media content to calibrate new users. Note that this method minimizes the amount of recorded user calibrations the content provider has to perform, since they would only need to create one video with calibrated data. Afterward, as more and more people view their videos, a provider can, over time, have its entire library correlated with gaze key points to be used for automatic calibration and gaze content recognition (such as product placement content viewed).

Figure 19:
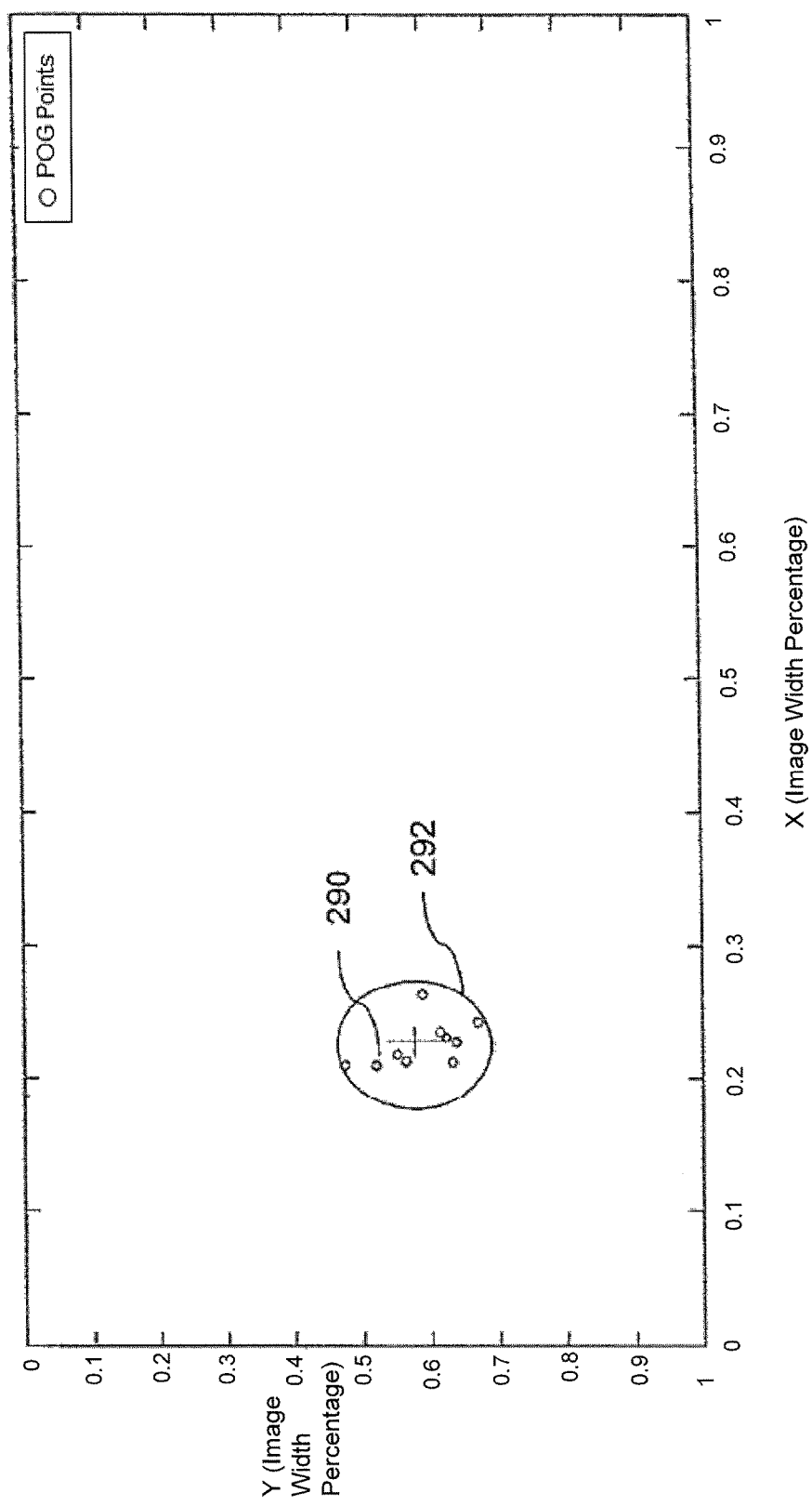
FIG. 19 shows a sample frame of video content with a number of recorded POGs, wherein a fixation point is apparent.

In FIG. 19, a sample video scene with the POG 290 of recorded users is displayed. These items are evaluated to determine the common gaze location 292. In the particular case where there are more than one possible key point 17 in a particular instance of time (for example if two faces are on the screen at one time and are equally attractive to the viewer's gaze), methods such as learning clustering can be used to differentiate them. The motion and direction of the viewer's gaze can lead to knowledge of which fixation point he or she is looking at.

Figure 20:
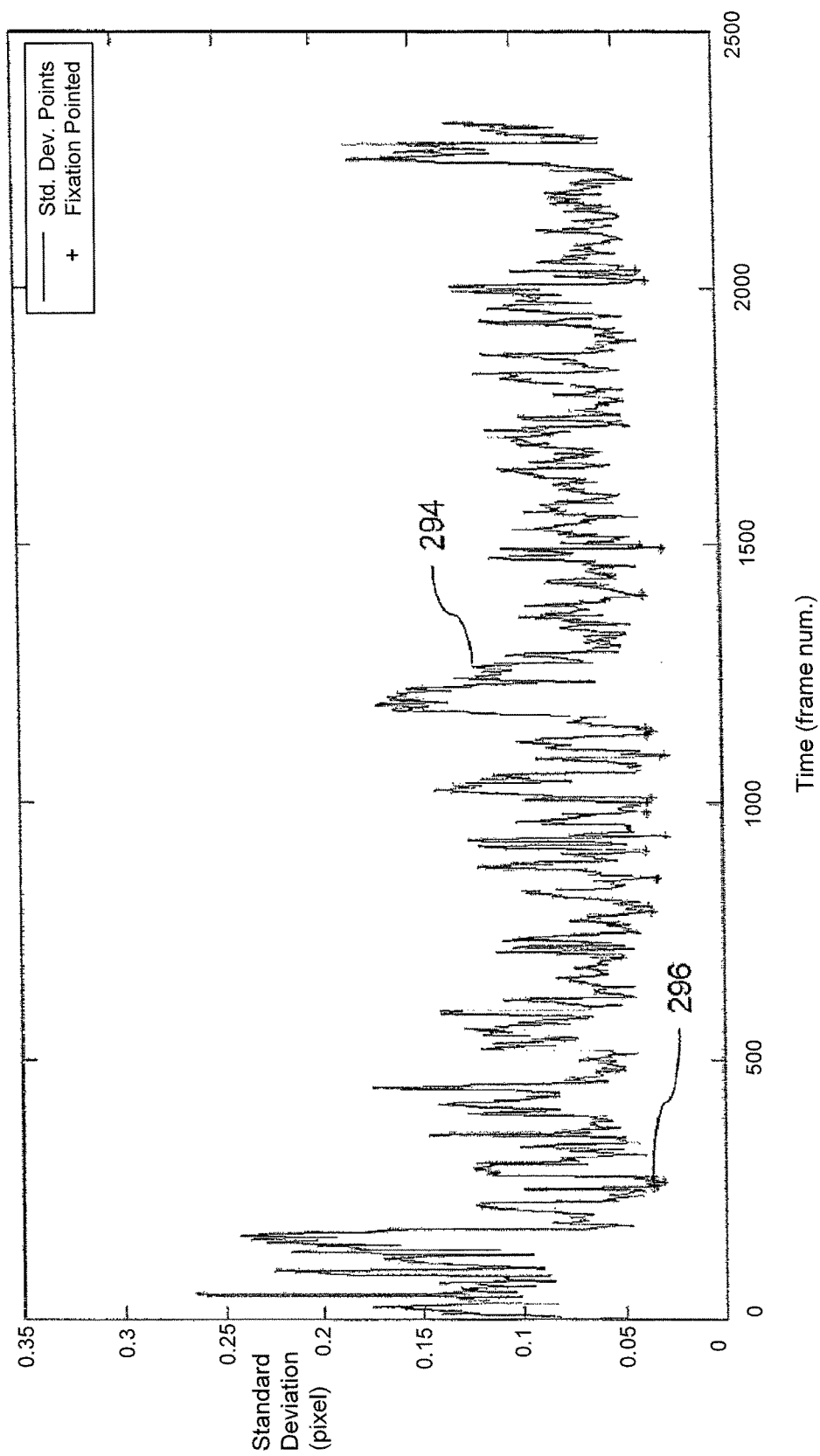
FIG. 20 is a graph of standard deviation on a per frame basis of a sample video, with potential fixation points delineated.

FIG. 20 shows a graph of the X and Y averaged standard deviations 294 of a group of viewers while watching a video. Selected key points 296 are the minima, thresholded below a variance value and above a minimum count of recorded users at a given time instance.

Instead of using key points that are found using face tracking or other content recognition techniques, key points could be inferred with a statistical analysis of the point of gazes obtained using the calibration. FIG. 17, discussed above, may be referred to in order to illustrate this principle, by showing calibrated and uncalibrated POGs from a particular user's viewing of media content in which the center of the screen shows the content of highest interest.

Given what is known in the context of the user is using the system, gaze points could be compared with the average patterns known for these contexts. An example of this would be collecting uncalibrated data of a user watching a television show. Televisual content 250 is usually made with most of the eye grabbing feature in an area comprising about two-thirds of the screen in an area a bit above the center 252 of the screen. From data acquired with multiple calibrated users, it can be seen that about 90% of the gaze data are contained inside the area mentioned previously.

It has been found that one can choose arbitrarily uncalibrated gaze data 256 and to try calibrations with a set of calibration points equally distributed over the screen using points 260. An exhaustive search is performed in which the gaze data using every calibration points is made. Each calibration is then tested using a sample of the uncalibrated gaze data 256 for a period where the user is exposed to the known media, in this case a TV show. A number of the calibrations returning the gaze point that corresponds as closely as possible to the average gaze 254 set are kept for further iterations.

The subsequent iteration consists in applying the same process but using new arbitrarily distributed points. For each calibration the uncalibrated gaze points associated to a precedent point is reused with all the newly chosen calibration point equally distributed around the previous point. The calibrations that return gaze data that most closely match average data for the context are kept for more iteration until we obtain small enough variance between different calibration point that it can be assumed that the precision is good enough.

Since there is a relation between the features detected by an eye tracking system and the gaze points calculated on the screen some preprocessing of this data could be done to ensure that the iterative process converge faster, has an higher chance of giving a good calibration and that some calibration points can be excluded for the first couple iterations.

The same statistical analysis could be done on the raw features detected in the eye to ensure to have well distributed gaze points around the screen.

In the example mentioned above, the raw features that comprise 90% of the data and the outliers could be eliminated and the in the uncalibrated gaze data left, the ones chosen could be the ones furthest apart to make sure to have points distributed everywhere around the screen. The iterative auto calibration function can then be applied to calibrate the user in a transparent way.

Figure 21:
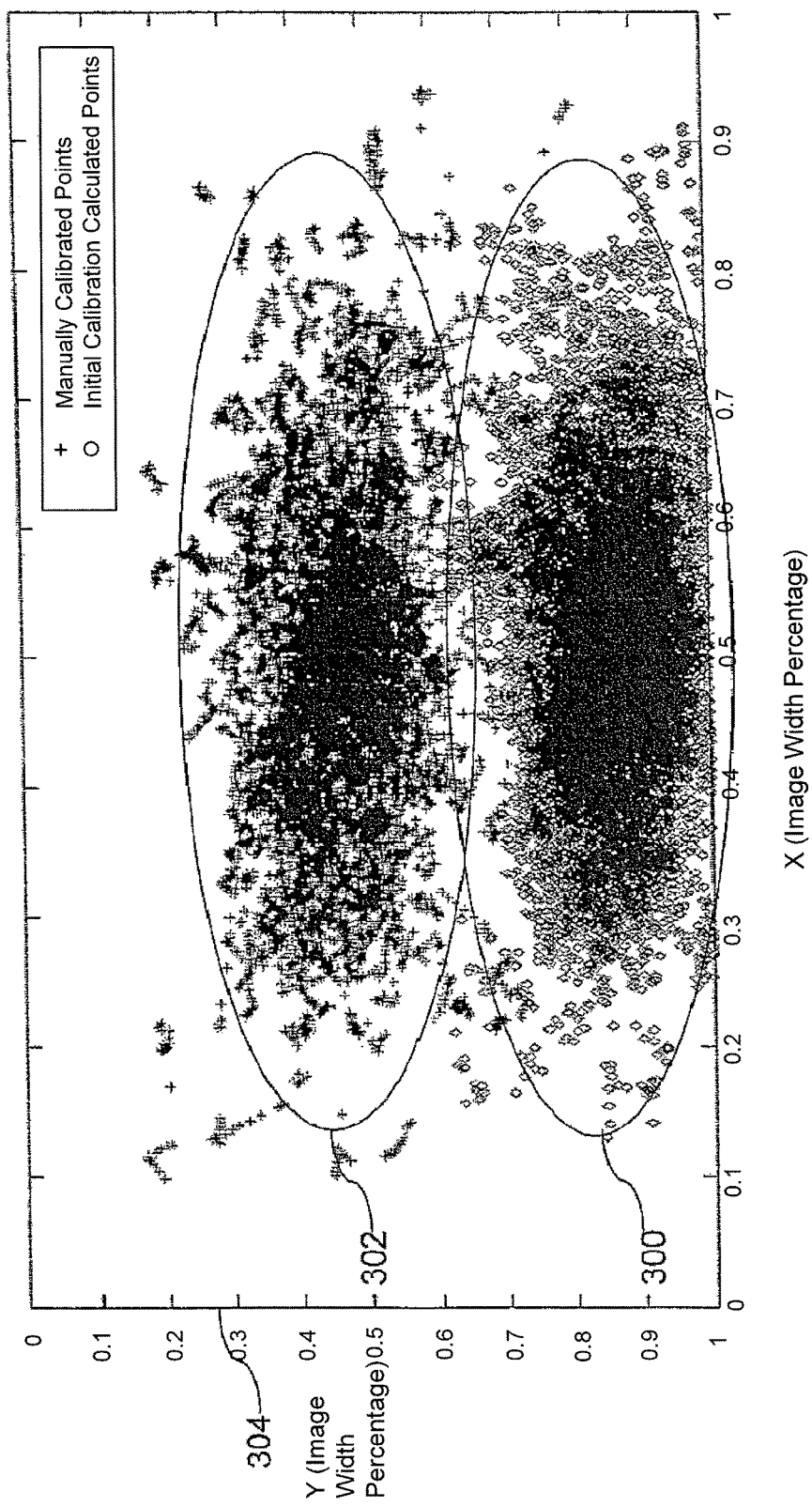
FIG. 21 illustrates a sample frame of video content containing a fixation point, user's current POG estimate, and a calculated central point for both a manual calibration and using an initial calibration.

FIG. 21 shows a sample collection of a user's POG estimates over a video frame 304. Baseline or uncalibrated data 300 is shown offset from the middle of the display. After calibration the gaze data 302 is shown centered on the display as expected when viewing TV and other video content.

A slightly alternate automatic calibration method takes full advantage of the pupil properties mentioned previously by, rather than calculating the user's pupil properties via a new calibration, modifying the initial calibration. It may use the same methods described previously for determining key points and accepting/rejecting said points as valid/invalid, but can use as few as two valid key points to create a mapping from initial calibration to accurate user calibration. This is because, with at least two points separate on both x and y axis, enough data is available to create the linear mapping to correct the offset and scaling between the two calibrations.

Figure 22:
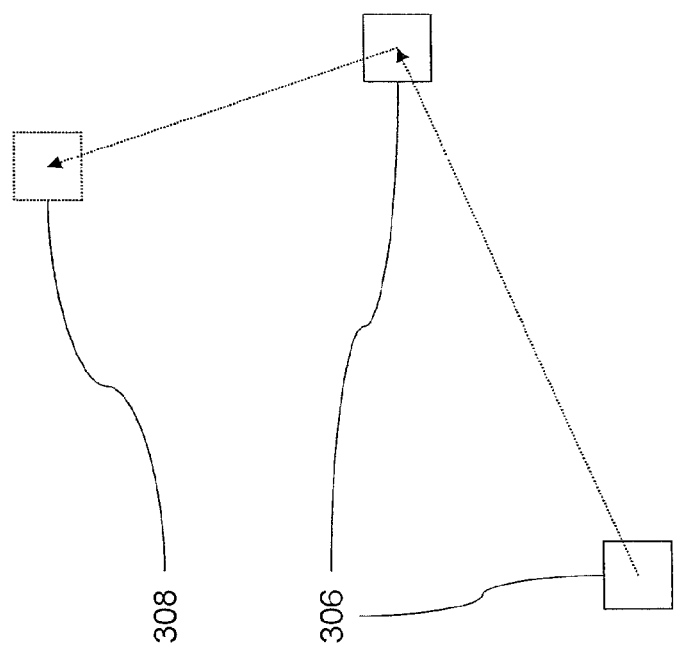
FIG. 22 shows a sample user interface for unlocking media content with gaze information.

FIG. 22 demonstrates a sample calibration interface which can be masked as an unlocking interface for beginning to use an application. By providing two points 306 disparate in both x and y coordinates, one can obtain both scaling and offset differences between the user's pupil parameters and those of the initial calibration. A third point 308 shown in FIG. 22 may then be used to test and confirm that the calibration is correct. In order to ensure the user hasn't merely looked at random points on the screen with the same spatial relationship, the third point could be chosen randomly and modified each time the unlock interface is summoned.

It will be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the environment 10, any component of or related to the display 14, gaze tracking system 20, media system 22, auto-calibration system 24, etc., or accessible or connectable thereto. Any application or module herein described may be implemented using computer readable/executable instructions that may be stored or otherwise held by such computer readable media.

The steps or operations in the flow charts and diagrams described herein are just for example. There may be many variations to these steps or operations without departing from the principles discussed above. For instance, the steps may be performed in a differing order, or steps may be added, deleted, or modified.

Although the above principles have been described with reference to certain specific examples, various modifications thereof will be apparent to those skilled in the art as outlined in the appended claims.

The invention claimed is:

1. A method of calibrating an eye gaze tracking system, the method comprising:
    applying an existing pre-calibration to obtain gaze data over a period of time during which content is being displayed;
    during the period of time, obtaining at least two key points corresponding to a portion of the content being displayed during the period of time, wherein the at least two key points change in and with the content during the period of time, wherein the changes to the at least two key points in and with the content comprise any one or more of appearing, disappearing, and transforming within the content during the period of time the content is being displayed, independent of user input;
    mapping the gaze data to the at least two key points that change within the content during the period of time the content is being displayed, wherein the mapping comprises correlating the gaze data to a spatial and temporal relationship between the at least two key points, and to the existing pre-calibration; and
    generating one or more calibration parameters using the mapping of the gaze data to the at least two key points that change within the content during the period of time the content is being displayed.

2. The method of claim 1, further comprising applying the one or more calibration parameters to the gaze data to generate calibrated gaze data; and providing the calibrated gaze data as an output.

3. The method of claim 1, further comprising updating a calibration profile using the one or more calibration parameters.

4. The method of claim 1, wherein the existing pre-calibration is an initial or default calibration.

5. The method of claim 1, wherein each key point is represented using a key record.

6. The method of claim 5, wherein the key record comprises a key point identifier, a timestamp, a position, and a size.

7. The method of claim 1, wherein the at least two key points are pre-associated with the media content.

8. The method of claim 1, wherein the at least two key points are generated according to the media content.

9. The method of claim 8, wherein the at least two key points are generated by searching for a commonality of points of gaze of different users to find fixation points common to at least some of the users.

10. The method of claim 9, wherein the fixation points are filtered to find key points based on the variance and number of users associated with a particular fixation point.

11. The method of claim 8, wherein the key points are generated using any one or more of feature tracking, motion tracking, and change in brightness.

12. The method of claim 11, wherein feature tracking comprises tracking any one or more of a face, eyes, and a mouth.

13. The method of claim 11, wherein the motion tracking comprises tracking one or more fast moving objects.

14. The method of claim 1, wherein the at least two key points are generated by modifying the media content.

15. The method of claim 1, wherein the at least two key points are determined by detecting a user interaction.

16. The method of claim 15, wherein the user interaction comprises selection on a display.

17. The method of claim 1, wherein linking the gaze data to the at least two key points comprises determining a time lag between a computed point of gaze and an associated key point and applying the time lag to align the gaze data with the at least two key points.

18. The method of claim 1, wherein generating the one or more calibration parameters comprises, selecting a subset of the at least two key points, and determining the accuracy of computed points of gaze for each key point.

19. The method of claim 1, wherein the at least two key points are generated by:
    recording points of gaze while displaying media content;
    calculating potential key points;
    using a measure of reliability to determine a filtered set of key points; and
    using a spatial distribution model to select key points to be used.

20. The method of claim 19, wherein the at least two key points are filtered based on knowledge of a direction of gaze calculated using an initial calibration.

21. The method of claim 1, wherein a calibration is determined via a linear mapping of an initial calibration to a final calibration, using key points to determine scaling and offset differences.

22. The method of claim 1, wherein a calibration is determined, without previous knowledge of x and y coordinates of points on the screen, by:
- calibrating a user using a plurality of combinations of random raw gaze data point and one or more arbitrarily distributed points on the screen;
- keeping at least one calibration that provides calibrated data fitting a viewing pattern of a known stimulus; and
- repeating the method iteratively using at least one new arbitrarily distributed point around points paired with each raw gaze data.

23. A non-transitory computer readable storage medium comprising computer executable instructions for calibrating an eye gaze tracking system, the computer executable instructions comprising instructions for:
- applying an existing pre-calibration to obtain gaze data over a period of time during which content is being displayed;
- during the period of time, obtaining at least two key points corresponding to a portion of the content being displayed during the period of time, wherein the at least two key points change in and with the content during the period of time, wherein the changes to the at least two key points in and with the content comprise any one or more of appearing, disappearing, and transforming within the content during the period of time the content is being displayed, independent of user input;
- mapping the gaze data to the at least two key points that change within the content during the period of time the content is being displayed, wherein the mapping comprises correlating the gaze data to a spatial and temporal relationship between the at least two key points, and to the existing pre-calibration; and
- generating one or more calibration parameters using the mapping of the gaze data to the at least two key points that change within the content during the period of time the content is being displayed.

24. A system comprising a processor and memory, the memory comprising computer executable instructions for calibrating an eye gaze tracking system, the computer executable instructions comprising instructions for:
- applying an existing pre-calibration to obtain gaze data over a period of time during which content is being displayed;
- during the period of time, obtaining at least two key points corresponding to a portion of the content being displayed during the period of time, wherein the at least two key points change in and with the content during the period of time, wherein the changes to the at least two key points in and with the content comprise any one or more of appearing, disappearing, and transforming within the content during the period of time the content is being displayed, independent of user input;
- mapping the gaze data to the at least two key points that change within the content during the period of time the content is being displayed, wherein the mapping comprises correlating the gaze data to a spatial and temporal relationship between the at least two key points, and to the existing pre-calibration; and
- generating one or more calibration parameters using the mapping of the gaze data to the at least two key points that change within the content during the period of time the content is being displayed.

* * * * *